(12) United States Patent
Lubisch et al.

(10) Patent No.: US 6,630,493 B1
(45) Date of Patent: Oct. 7, 2003

(54) HETEROCYCLICALLY SUBSTITUTED AMIDES, THEIR PREPARATION AND USE

(75) Inventors: Wilfried Lubisch, Heidelberg (DE); Achim Möller, Grünstadt (DE); Hans-Jörg Treiber, Brühl (DE); Monika Knopp, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/673,087

(22) PCT Filed: Apr. 19, 1999

(86) PCT No.: PCT/EP99/02611

§ 371 (c)(1),
(2), (4) Date: Oct. 11, 2000

(87) PCT Pub. No.: WO99/54304

PCT Pub. Date: Oct. 28, 1999

(30) Foreign Application Priority Data

Apr. 20, 1998 (DE) .......................... 198 17 459

(51) Int. Cl.⁷ .................. A01N 43/40; A61K 31/44; C07D 213/46; C07D 211/72; C07D 211/78
(52) U.S. Cl. .................. 514/354; 514/355; 546/314; 546/316; 546/323
(58) Field of Search .................. 546/314, 316, 546/323; 544/406; 548/200, 333.5, 341.5; 514/354, 355

(56) References Cited

FOREIGN PATENT DOCUMENTS

| DE | 196 42591 | 4/1998 |
|---|---|---|
| EP | 520 336 | 12/1992 |
| WO | 91/09801 | 7/1991 |
| WO | 92/11850 | 7/1992 |
| WO | 92/12140 | 7/1992 |
| WO | 94/00095 | 1/1994 |
| WO | 96/06211 | 2/1996 |
| WO | 97/21690 | 6/1997 |
| WO | 98/16512 | 4/1998 |
| WO | 98/41092 | 9/1998 |
| WO | 98/41506 | 9/1998 |

OTHER PUBLICATIONS

Bio.Chem.Res.Com., vol. 158,No. 2,1989, McGowan et al.
J.Med.Chem., 1990,33,11–13.
J.Med.Chem., Jan. 24, 1992, vol. 35, No. 2, Angliker et al., 216–220.
Chem.Soc.Japan, No.2, 1990, Matsueda et al., 191–194.
TIBS16–4/91,Mehdi, 150–153.
JP 08183771, Abstract.
J.Med.CHem,1993,36,3472–3480, Li et al.
J.Med.Chem, Sep. 2, 1994,vol. 37, No. 18,Harbeson et al.
Tet.Ltr., vol. 29,No. 28,pp3433–3436, 1988, Burkhart et al.

*Primary Examiner*—Richard L. Raymond
*Assistant Examiner*—Zachary C. Tucker

(57) ABSTRACT

Amides of the general formula I

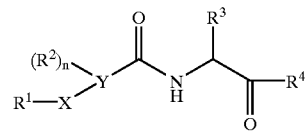

and their tautomeric and isomeric forms, possible enantiomeric and diastereomeric forms, as well as possible physiologically tolerable salts, in which the variables have the meanings stated in the description, their preparation and use as calpain inhibitors.

15 Claims, No Drawings

HETEROCYCLICALLY SUBSTITUTED AMIDES, THEIR PREPARATION AND USE

This application was filed under 35 U.S.C. 371, and is the U.S. National Stage of PCT/EP99/02611, filed Apr. 19, 1999.

The present invention relates to novel amides, which are inhibitors of enzymes, in particular cysteine proteases, such as calpain (=calcium-dependent cysteine proteases) and its isoenzymes, and cathepsins, for example B and L.

Calpains are intracellular, proteolytic enzymes from the so-called cysteine proteases group and are found in many cells. Calpains are activated by an increased calcium concentration, a differentiation being made between calpain I or μ-calpain, which is activated by μ-molar concentrations of calcium ions, and calpain II or m-calpain, which is activated by m-molar concentrations of calcium ions (P. Johnson, Int. J. Biochem. 1990, 22(8), 811–22). Still further calpain isoenzymes are postulated today (K. Suzuki et al., Biol. Chem. Hoppe-Seyler, 1995, 376(9), 523–9).

It is suspected that calpains play an important part in various physiological processes. These include cleavage of regulatory proteins such as protein kinase C, cytoskeletal proteins such as MAP 2 and spectrin, muscle proteins, protein breakdown in rheumatoid arthritis, proteins in the activation of platelets, neuropeptide metabolism, proteins in mitosis and others which are listed in M. J. Barrett et al., Life Sci. 1991, 48, 1659–69 and K. K. Wang et al., Trends in Pharmacol. Sci., 1994, 15, 412–9.

Increased calpain levels have been measured in various pathophysiological processes, for example: ischemias of the heart (e.g. cardiac infarct), of the kidney or of the central nervous system (e.g. "stroke"), inflammations, muscular dystrophy, cataracts of the eyes, injuries to the central nervous system (e.g. trauma), Alzheimer's disease etc. (see K. K. Wang, above). A relationship of these diseases with increased and lasting intracellular calcium levels is suspected. As a result, calcium-dependent processes are overactivated and are no longer subject to physiological regulation. Accordingly, overactivation of calpains can also initiate pathophysiological processes.

It was therefore postulated that inhibitors of the capain enzymes can be useful for the treatment of these diseases. Various investigations confirm this. Thus Seung-Chyul Hong et al., Stroke 45 1994, 25(3), 663–9 and R. T. Bartus et al., Neurological Res. 1995, 17, 249–58 have shown a neuroprotective action of calpain inhibitors in acute neurodegenerative disorders or ischemias, such as occur after cerebral stroke. Likewise, after experimental brain traumata, calpain inhibitors improved recovery from the memory power deficits and neuromotor disorders which occurred (K. E. Saatman et al. Proc. Natl. Acad. Sci. USA, 1996, 93,3428–3433). C. L. Edelstein et al., Proc. Natl. Acad. Sci. USA, 1995, 92, 7662–6, found a protective action of calpain inhibitors on kidneys damaged by hypoxia. Yoshida, Ken Ischi et al., Jap. Circ. J. 1995, 59(1), 40–8, were able to show favorable effects of calpain inhibitors after cardiac damage which was produced by ischemia or reperfusion. Since calpain inhibitors inhibit the release of the β-AP4 protein, potential use as a therapeutic for Alzheimer's disease was proposed (J. Higaki et al., Neuron, 1995, 14, 651–59). The release of interleukin-1α is also inhibited by calpain inhibitors (N. Watanabe et al., Cytokine 1994, 6(6), 597–601). It was furthermore found that calpain inhibitors show cytotoxic effects on tumor cells (E. Shiba et al., 20th Meeting Int. Ass. Breast Cancer Res., Sendai Jp, Sep. 25–28 1994, Int. J. Oncol. 5(Suppl.), 1994, 381).

Further possible uses of calpain inhibitors are listed in K. K. Wang, Trends in Pharmacol. Sci., 1994, 15, 412–8.

Calpain inhibitors have already been described in the literature. These are mainly, however, either irreversible or peptide inhibitors. As a rule, irreversible inhibitors are alkylating substances and have the disadvantage that they react nonselectively in the body or are unstable. Thus these inhibitors often show undesirable side effects, such as toxicity, and are accordingly restricted in their use or unutilizable. Among the irreversible inhibitors can be included, for example, the epoxides E 64 (E. B. McGowan et al., Biochem. Biophys. Res. Commun. 1989, 158, 432–5), α-haloketones (H. Angliker et al., J. Med. Chem. 1992, 35, 216–20) or disulfides (R. Matsueda et al., Chem. Lett. 1990, 191–194).

Many known reversible inhibitors of cysteine proteases, such as calpain, are peptide aldehydes, in particular dipeptide and tripeptide aldehydes such as, for example, Z-Val-Phe-H (MDL 28170) (S. Mehdi, Tends [sic] in Biol. Sci. 1991, 16, 150–3). Under physiological conditions, peptide aldehydes have the disadvantage that they are often unstable on account of the great reactivity, can be rapidly metabolized and are prone to nonspecific reactions which can be the cause of toxic effects (J. A. Fehrentz and B. Castro, Synthesis 1983, 676–78).

In JP 08183771 (CA 1996, 605307) and in EP 520336, aldehydes which are derived from 4-piperidinoylamides and 1-carbonylpiperidino-4-ylamides have been described as calpain inhibitors. In WO 97/21690, aldehydes derived from N-sulfonylprolinamide were prepared. WO 96/06211 describes an aldehyde derivative analogous to the general structure I, but where Y is a xanthine derivative which does not carry any further radicals such as $R^1$-X. However, the aldehydes claimed here, which are derived from heteroaromatically substituted amides of the general structure I, have never previously been described.

Peptide ketone derivatives are also inhibitors of cysteine proteases, in particular calpains. Thus, for example, in the case of serine proteases ketone derivatives are known as inhibitors, the keto group being activated by an electron-withdrawing group such as $CF_3$. In the case of cysteine proteases, derivatives with ketones activated by $CF_3$ or similar groups are not very active or inactive (M. R. Angelastro et al., J. Med. Chem. 1990, 33, 11–13). Surprisingly, in the case of calpain hitherto only ketone derivatives, in which, on the one hand, leaving groups in the α-position cause an irreversible inhibition and, on the other hand, a carboxylic acid derivative activates the keto group, were found to be effective inhibitors (see M. R. Angelastro et al., see above; WO 92/11850; WO 92,12140; WO 94/00095 and WO 95/00535). However, of these ketoamides and ketoesters, hitherto only peptide derivatives have been described as effective (Zhaozhao Li et al., J. Med. Chem. 1993, 36, 3472–80; S. L. Harbenson et al., J. Med. Chem. 1994, 37, 2918–29 and see above M. R. Angelastro et al.).

Ketobenzamides are already known in the literature. Thus the keto ester PhCO—Abu—$COOCH_2CH_3$ was described in WO 91/09801, WO 94/00095 and WO 92/11850. The analogous phenyl derivative Ph—CONH—CH($CH_2$Ph)—CO—$COOCH_3$ was found in M. R. Angelastro et al., J. Med. Chem. 1990, 33, 11–13 to be, however, only a weak calpain inhibitor. This derivative is also described in J. P. Burkhardt, Tetrahedron Lett., 1988, 3433–36. The significance of the substituted benzamides, however, has never been investigated until now.

In the present invention, substituted nonpeptide aldehydes, ketocarboxylic acid esters and ketoamide derivatives were described. These compounds are new and surprisingly show the possibility of obtaining potent nonpeptide inhibitors of cysteine proteases, such as, for example, calpain, by incorporation of rigid structural fragments.

The present invention relates to heterocyclically substituted amides of the general formula I

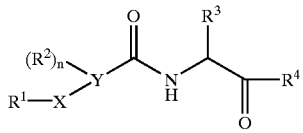

and their tautomeric and isomeric forms, possible enantiomeric and diastereomeric forms, as well as possible physiologically tolerable salts, in which the variables have the following meanings:

$R^1$ can be phenyl, naphthyl, quinolyl, pyridyl, pyrimidyl, pyrazyl, pyridazyl, imidazolyl, thiazole, quinazyl, isoquinolyl, quinazyl, quinoxalyl, thienyl, benzothienyl, benzofuranyl, furanyl, and indolyl, where the rings can be additionally substituted by up to 3 radicals $R^5$, $R^2$ is chlorine, bromine, fluorine, $C_1$–$C_6$-alkyl, $C_1$–$C_6$-alkenyl, $C_1$–$C_6$-alkynyl, $C_1$–$C_6$-alkylphenyl, $C_1$–$C_6$-alkenylphenyl, $C_1$–$C_6$-alkynylphenyl, phenyl, NHCO—$C_1$–$C_4$-alkyl, NHSO$_2$—$C_1$–$C_4$-alkyl, —NHCOphenyl, —NHCO-naphthyl, NO$_2$, —O—$C_1$–$C_4$-alkyl and NH$_2$, where the aromatic rings can additionally carry one or two radicals $R^5$ and two radicals $R^2$ together can also be a chain —CH=CH—CH=CH— and thus form a fused benzo ring, which for its part can be substituted by one $R^5$ and $R^3$ is —$C_1$–$C_6$-alkyl, which is branched or unbranched, and which can additionally carry an S—CH$_3$ radical or a phenyl, cyclohexyl, cycloheptyl, cyclopentyl, indolyl, pyridyl or naphthyl ring which for its part can be substituted by by at most two radicals $R^5$, where $R^5$ is hydrogen, $C_1$–$C_4$-alkyl, which is branched or unbranched, —O—$C_1$–$C_4$-alkyl, OH, Cl, F, Br, I, CF$_3$, NO$_2$, NH$_2$, CN, COOH, COO—$C_1$–$C_4$-alkyl, —NHCO—$C_1$–$C_4$-alkyl, —NHCO—phenyl, —NHSO$_2$—$C_1$–$C_4$-alkyl, —NHSO$_2$-phenyl, —SO$_2$—$C_1$–$C_4$-alkyl, —(CH$_2$)$_n$—NR$^{12}$R$^{13}$ and —SO$_2$-phenyl;

X is a bond, —(CH$_2$)$_m$—, —(CH$_2$)$_m$—O—(CH$_2$)$_o$—, —(CH$_2$)$_o$—S—(CH2)$_m$—, —(CH$_2$)$_o$—SO—(CH$_2$)$_m$—, —(CH$_2$)$_o$—SO$_2$—(CH$_2$)$_m$—, —CH=CH—, —C≡C—, —CO—CH=CH—, —(CH$_2$)$_o$—CO—(CH$_2$)$_m$—, —(CH$_2$)$_m$—NHCO—(CH$_2$)$_o$—, —(CH$_2$)$_m$—CONH—(CH$_2$)$_m$—, —(CH$_2$)$_m$—NHSO$_2$—(CH$_2$)$_o$—, —NH—CO—CH=CH—, —(CH$_2$)$_m$—SO$_2$NH—(CH$_2$)$_o$—, —CH=CH—CONH— and

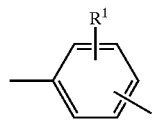

and in the case of CH=CH double bonds can be either the E or the Z form and $R^1$-X together are also

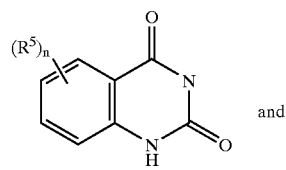

and

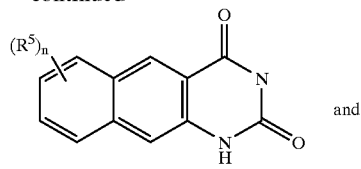

and

Y is an unsaturated heterocyclic ring such as pyridine, pyrimidine, pyrazine, imidazole and thiazole and $R^4$ is hydrogen, COOR$^6$ and CO—Z, in which Z is NR$^7$R$^8$, and is

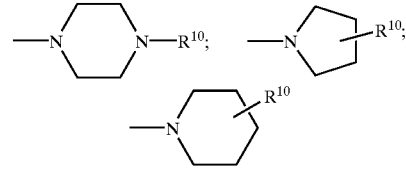

$R^6$ is hydrogen, $C_1$–$C_6$-alkyl, which is linear or branched, and which can be substituted by a phenyl ring which itself can additionally be substituted by one or two radicals $R^9$, and $R^7$ is hydrogen, $C_1$–$C_6$-alkyl, which is branched and unbranched, and $R^8$ is hydrogen, $C_1$–$C_6$-alkyl, which is branched or unbranched, which can additionally be substituted by a phenyl ring which can additionally carry a radical $R^9$, and by

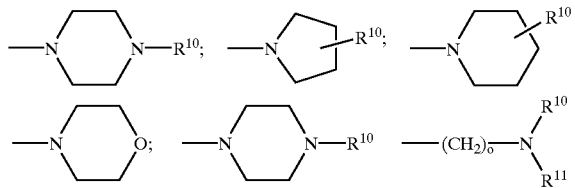

and $R^9$ can be hydrogen, $C_1$–$C_4$-alkyl, which is branched or unbranched, —O—$C_1$–$C_4$-alkyl, OH, Cl, F, Br, I, CF$_3$, NO$_2$, NH$_2$, CN, COOH, COO—$C_1$–$C_4$-alkyl, —NHCO—$C_1$–$C_4$-alkyl, —NHCO—phenyl, —NHSO$_2$—$C_1$–$C_4$-alkyl, —NHSO$_2$-phenyl, —SO$_2$—$C_1$–$C_4$-alkyl and —SO$_2$-phenyl $R^{10}$ is hydrogen, $C_1$–$C_6$-alkyl, which is linear or branched, and which can be substituted by a phenyl ring which itself can additionally be substituted by one or two radicals $R^9$, and $R^{11}$ is hydrogen, $C_1$–$C_6$-alkyl, which is linear or branched, and which can be substituted by a phenyl ring which itself can additionally be substituted by one or two radicals $R^9$, and n is a number 0, 1 or 2, and m,o independently of one another is a numeral 0, 1, 2, 3 or 4.

The compounds of the formula I can be employed as racemates, as enantiomerically pure compounds or as diastereomers. If enantiomerically pure compounds are desired, these can be obtained, for example, by carrying out a classical racemate resolution with the compounds of the formula I or their intermediates using a suitable optically active base or acid. On the other hand, the enantiomeric compounds can also be prepared by use of commercially obtainable compounds, for example optically active amino acids such as phenylalanine, tryptophan and tyrosine.

The present invention also relates to compounds which are mesomeric or tautomeric with compounds of the formula I, for example those in which the aldehyde or keto group of the formula I is present as an enol tautomer.

The present invention further relates to the physiologically tolerable salts of the compounds I, which can be obtained by reaction of compounds I with a suitable acid or base. Suitable acids and bases are listed, for example, in Fortschritte der Arzneimittelforschung, 1996, Birkhäuser Verlag, Vol. 10, pp. 224–285. These include, for example, hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid etc. or sodium hydroxide, lithium hydroxide, potassium hydroxide, α,α,α-tris (hydroxymethyl)methylamine, triethylamine etc.

The amides I according to the invention can be prepared in various ways, which have been outlined in the synthesis scheme.

is then converted to the amides IV using amines. The reaction is carried out in anhydrous, inert solvents such as methylene chloride, tetrahydrofuran and dimethylformamide at temperatures from −20 to +25° C.

These alcohol derivatives IV can be oxidized to the aldehyde derivatives I according to the invention. It is possible to use various customary oxidation reactions for this (see C. R. Larock, Comrenhensive Organic Transformations, VCH Publisher, 1989, page 604 f.) such as, for example, Swern and Swern-analogous oxidations (T. T. Tidwell, Synthesis 1990, 857–70), sodium hypochloride/TEMPO (S. L. Harbenson et al., see above) or Dess-Martin (J. Org. Chem. 1983, 48, 4155). Preferably, here the reaction is carried out in inert aprotic solvents such as dimethylformamide, tetrahydrofuran or methylene chloride using oxidants such as $DMSO/pyxSO_3$ or DMSO/oxalyl chloride at temperatures from −50 to +25° C., depending on the method (see above references).

Alternatively, the carboxylic acid II can be reacted with aminohydroxamic acid derivatives VI to give benzamides VII. In this case, use is made of the same reaction procedure as in the preparation of IV. The hydroxamic [lacuna] deriva-

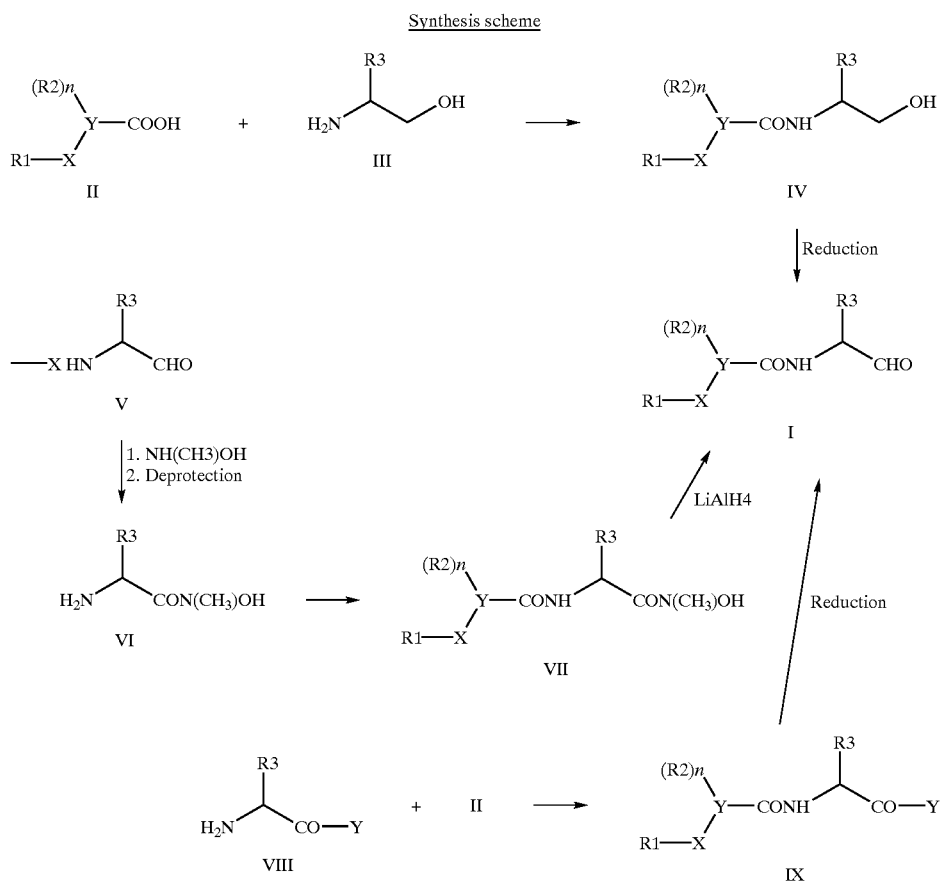

Synthesis scheme

Heterocyclic carboxylic acids II are linked to suitable aminoalcohols III to give the corresponding amides IV. Use is made here of customary peptide coupling methods, which are mentioned either in C. R. Larock, Comprehensive Organic Transformations, VCH Publisher, 1989, page 972f. or in Houben-Weyl, Methoden der organischen Chemie [Methods of organic Chemistry], 4th Edition, E5, Chap. V. The reaction is preferably carried out using "activated" acid derivatives of II, the acid group COOH being converted into a group COL. L is a leaving group such as, for example, Cl, imidazole and N-hydroxybenzotriazole. This activated acid tives VI are obtainable from the protected amino acids V by reaction with a hydroxylamine. In this process, use is also made here of an amide preparation process which has already been described. The removal of the protective group X, for example Boc, is carried out in the customary manner, for example using trifluoroacetic acid. The amidohydroxamic acids VII thus obtained can be converted into the aldehydes I according to the invention by reduction. In this process, use is made, for example, of lithium aluminum hydride as a reductant at temperatures from −60 to 0° C. in inert solvents such as tetrahydrofuran or ether.

Analogously to the last process, carboxylic acids or acid derivatives, such as esters IX (Y=COOR', COSR') can also be prepared, which can likewise be converted into the aldehydes I according to the invention by reduction. These processes are listed in R. C. Larock, Comprehensive Organic Transformations, VCH Publisher, 1989, page 619–26.

The preparation of the heterocyclically substituted amides I according to the invention, [lacuna] carry a ketoamide or ketoester group, can be carried out in various ways, which have been outlined in synthesis schemes 2 and 3.

If appropriate, the carboxylic acid esters IIa are converted into the acids II using acids or bases such as lithium hydroxide, sodium hydroxide or potassium hydroxide in aqueous medium or in mixtures of water and organic solvents such as alcohols or tetrahydrofuran at room temperature or elevated temperatures, such as 25–100° C.

These acids II are linked to an α-amino acid derivative, customary conditions being used, which are listed, for example, in Houben-weyl, Methoden der organischen Chemie [Methods of Organic Chemistry], 4th Edition, E5, Chap. V, and C. R. Larock, Comprehensive Organic Transformations, VCH Publisher, 1989, Ch.

For example, the carboxylic acids II are converted into the "activated" acid derivatives IIb=Y-COL, where L is a leaving group such as Cl, imidazole and N-hydroxybenzotriazole, and are then converted into the derivative XI by addition of an amino acid derivative $H_2N$—$CH(R^3)$—COOR. This reaction is carried out in anhydrous, inert solvents such as methylene chloride, tetrahydrofuran and dimethylformamide at temperatures from −20 to +25° C.

Scheme 1

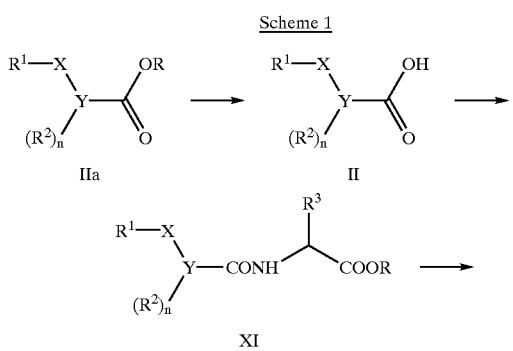

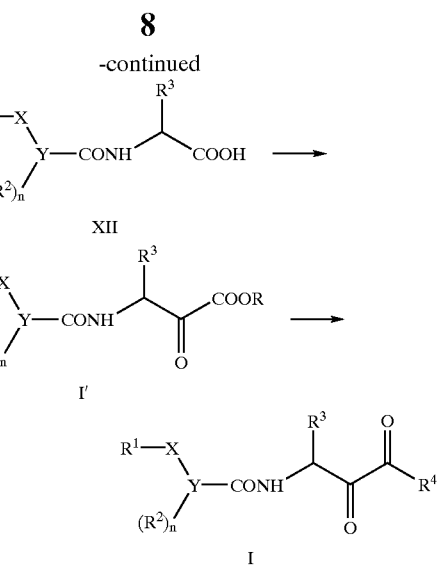

The derivatives XI, which as a rule are esters, are converted into the ketocarboxylic acids XII analogously to the hydrolysis described above. The ketoesters I' are prepared in a reaction analogous to that of Dakin-West, the reaction being carried out according to a method of ZhaoZhao Li et al., J. Med. Chem., 1993, 36, 3472–80. In this process, carboxylic acids such as XII are reacted with oxalic acid monoester chloride at elevated temperature (50–100° C.) in solvents, such as, for example, tetrahydrofuran and the products thus obtained are then reacted with bases such as sodium methoxide in ethanol at temperatures of 25–80° C. to give the ketoesters I' according to the invention. The ketoesters I' can be hydrolyzed as described above, for example to ketocarboxylic acids according to the invention.

The reaction to give ketobenzamides I' is also carried out analogously to the method of ZhaoZhao Li et al. (see above). The keto group in I' is protected by addition of 1,2-ethanedithiol under Lewis acid catalysis, such as, for example, boron trifluoride etherate, in inert solvents, such as methylene chloride, at room temperature, a dithian being obtained. These derivatives are reacted with amines $R^3$-H in polar solvents, such as alcohols, at temperatures of 0–80° C., the ketoamides I ($R^4$=Z or $NR^7R^8$) being obtained.

Scheme 2

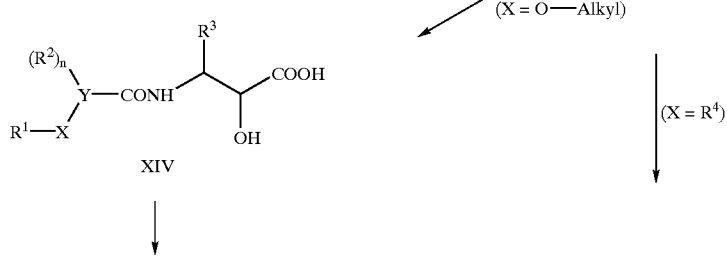

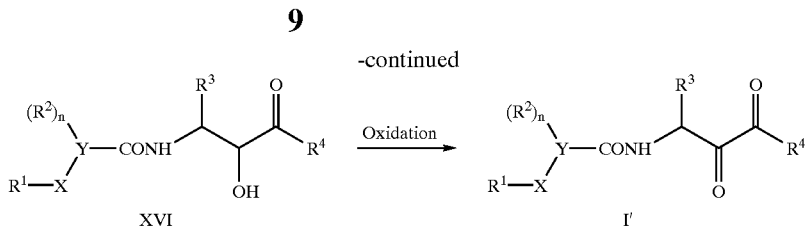

An alternative method is shown in scheme 2. The ketocarboxylic acids II are reacted with aminohydroxycarboxylic acid derivatives XIII (for preparation of XIII see S. L. Harbenson et al., J. Med. Chem. 1994, 37, 2918–29 or J. P. Burkhardt et al. Tetrahedron Lett. 1988, 29, 3433–3436) under customary peptide coupling methods (see above, Houben-Weyl), amides XIV being obtained. These alcohol derivatives XIV can be oxidized to the ketocarboxylic acid derivatives I according to the invention. Use can be made for this of various customary oxidation reactions (see C. R. Larock, Comprehensive Organic Transformations, VCH Publisher, 1989, page 604 f.) such as, for example, Swern and Swern-analogous oxidations, preferably dimethyl sulfoxide/pyridine-sulfur trioxide complex in solvents such as methylene chloride or tetrahydrofuran, if appropriate with addition of dimethyl sulfoxide, at room temperature or temperatures of −50 to 25° C. (T. T. Tidwell, Synthesis 1990, 857–70) or sodium hypochloride/TEMPO (S. L. Harbenson et al., see above).

If XIV are α-hydroxy esters (X=O-alkyl), these can be hydrolyzed to carboxylic acids XV, the reaction being carried out analogously to the above methods, but preferably using lithium hydroxide in water/tetrahydrofuran mixtures at room temperature. The preparation of other esters or amides XVI is carried out by reaction with alcohols or amines under coupling conditions which have already been described. The alcohol derivative XVI can be oxidized again to give ketocarboxylic acid derivatives I according to the invention.

The preparation of the carboxylic acid esters II have already been described in some cases or are carried out according to customary chemical methods.

Compounds in which X is a bond are prepared by customary aromatic coupling, for example the Suzuki coupling with boric acid derivatives and halides with palladium catalysis or copper-catalyzed coupling of aromatic halides. The alkyl-bridged radicals (X=—(CH$_2$)$_m$—) can be prepared by reduction of the analogous ketones or by alkylation of the organolithium, e.g. ortho-phenyloxazolidines, or other organometal compounds (cf. I. M. Dordor et al., J. Chem. Soc. Perkin Trans. I, 1984, 1247–52).

Ether-bridged derivatives are prepared by alkylation of the corresponding alcohols or phenols with halides.

The sulfoxides and sulfones are accessible by oxidation of the corresponding thioethers.

Alkene- and alkyne-bridged compounds are prepared, for example, by Heck reaction from aromatic halides and appropriate alkenes and alkynes (cf. I. Sakamoto et al., Chem. Pharm. Bull., 1986, 34, 2754–59).

The chalcones are formed by condensation of acetophenones with aldehydes and can optionally be converted into the analogous alkyl derivatives by hydrogenation.

Amides and sulfonamides are prepared from the amines and acid derivatives analogously to the methods described above.

The heterocyclically substituted amides I contained in the present invention are inhibitors of cysteine proteases, in particular cysteine proteases such as the calpains I and II and cathepsins B and L.

The inhibitory action of the heterocyclically substituted amides I was determined using enzyme tests customary in the literature, a concentration of the inhibitor at which 50% of the enzyme activity is inhibited (=IC$_{50}$) being determined as a scale of action. The amides I were measured in this manner for inhibitory action of calpain I, calpain II and cathepsin B.

Cathepsin B Test

The cathepsin B inhibition was determined analogously to a method by S. Hasnain et al., J. Biol. Chem. 1993, 268, 235–40.

2 μL of an inhibitor solution, prepared from inhibitor and DMSO (final concentrations: 100 μM to 0.01 μM), are [lacuna] to 88 μL of cathepsin B (cathepsin B from human liver (Calbiochem), diluted to 5 units in 500 μM buffer). This mixture is preincubated at room temperature (25° C.) for 60 minutes and the reaction is then started by addition of 10 μL of 10 mM Z-Arg-Arg-pNA (in buffer with 10% DMSO). The reaction is monitored at 405 nM in a microtiter plate reader for 30 minutes. The IC$_{50}$s are then determined from the maximum gradients.

Calpain I and II Test

The testing of the inhibitory properties of calpain inhibitors is carried out in buffer using 50 mM tris HCl, pH 7.5; 0.1 M NaCl; 1 mM dithiotreithol; 0.11 mM CaCl$_2$, the fluorogenic calpain substrate Suc-Leu-Tyr-AMC (25 mM dissolved in DMSO, Bachem/Switzerland) being used. Human μ-calpain is isolated from erythrocytes and, after several chromatographic steps (DEAE-Sepharose, phenyl-Sepharose, Superdex 200 and Blue Sepharose), enzyme having a purity of >95%, assessed according to SDS-PAGE, Western blot analysis and N-terminal sequencing, is obtained. The fluorescence of the cleavage product 7-amino-4-methylcoumarin (AMC) is monitored in a Spex-Fluorolog fluorimeter at λex=380 nm and λem=460 nm. In a measuring range of 60 min, the cleavage of the substrate is linear and the autocatalytic activity of calpain is low if the experiments are carried out at temperatures of 12° C. The inhibitors and the calpain substrate are added to the experimental batch as DMSO solutions, where DMSO should not exceed 2% in the final concentration.

In an experimental batch, 10 μl of substrate (250 μM final) and then 10 μl of μ-calpain (2 μg/ml final, i.e. 18 nM) are added to a 1 ml cuvette which contains buffer. The calpain-mediated cleavage of the substrate is measured for 15–20 min. 10 μl of inhibitor (50–100 μM solution in DMSO) are then added and the inhibition of the cleavage is measured for a further 40 min.

K$_i$ values are determined according to the classical equation for reversible inhibition:

Ki=I/(v0/vi)−1; where I=inhibitor concentration, v0=initial velocity before addition of the inhibitor; vi=reaction velocity in equilibrium.

The velocity is calculated from v=release of AMC/time i.e. height/time.

Calpain is an intracellular cysteine protease. Calpain inhibitors must pass through the cell membrane in order to prevent the breakdown of intracellular proteins by calpain. Some known calpain inhibitors, such as, for example, E 64 and leupeptin, only cross the cell membranes with difficulty and accordingly show, although they are good calpain inhibitors, only a poor action in cells. The aim is to find compounds having better membrane accessibility. As a demonstration of the membrane accessibility of calpain inhibitors, we use human platelets.

Calpain-mediated Breakdown of Tyrosine Kinase pp60src in Platelets

After the activation of platelets, the tyrosine kinase pp60src is cleaved by calpain. This was investigated in detail by Oda et al. in J. Biol. Chem., 1993, Vol 268, 12603–12608. It was shown in this context that the cleavage of pp60src can be prevented by calpeptin, an inhibitor of calpain. The cellular effectiveness of our substances was tested following this publication. Fresh human blood treated with citrate was centrifuged at 200 g for 15 min. The platelet-rich plasma was pooled and diluted 1:1 with platelet buffer (platelet buffer: 68 mM NaCl, 2.7 mM KCl, 0.5 MM $MgCl_2$ ×6 $H_2O$, 0.24 mM $NaH_2PO_4$×$H_2O$, 12 mM $NaHCO_3$, 5.6 mM glucose, 1 mM EDTA, pH 7.4). After a centrifugation and washing step with platelet buffer, the platelets were adjusted to $10^7$ cells/ml. The isolation of the human platelets was carried out at RT.

In the test batch, isolated platelets (2 H $10^6$) were preincubated at 37° C. with different concentrations of inhibitors (dissolved in DMSO) for 5 min. The platelets were then activated with 1 $\mu$M ionophore A23187 and 5 mM $CaCl_2$. After incubation for 5 min, the platelets were briefly centrifuged at 13000 rpm and the pellet was taken up in SDS sample buffer (SDS sample buffer: 20 mM tris HCl, 5 mM EDTA, 5 mM EGTA, 1 mM DTT, 0.5 mM PMSF, 5 $\mu$g/ml leupeptin, 10 $\mu$g/ml pepstatin, 10% glycerol and 1% SDS). The proteins were separated in a 12% strength gel and pp60src and its 52 kDa and 47 kDa cleavage products were identified by Western blotting. The polyclonal rabbit antibody anti-Cys-src ($pp60^{c-src}$) used was purchased from the company Biomol Feinchemikalien (Hamburg). This primary antibody was detected using an HRP-coupled second antibody from goats (Boehringer Mannheim, FRG). The Western blotting was carried out according to known methods.

The quantification of the cleavage of $pp60^{src}$ was carried out by densitometry, the controls used being nonactivated platelets (control 1: no cleavage) and platelets treated with ionophore and calcium (control 2: corresponds to 100% cleavage). The $ED_{50}$ value corresponds to the concentration of inhibitor at which the intensity of the color reaction is reduced by 50%.

Glutamate-induced Cell Death in Cortical Neurones

The test was carried out as in Choi D. W., Maulucci-Gedde M. A. and Kriegstein A. R., "Glutamate neurotoxicity in cortical cell culture". J. Neurosci. 1989, 7, 357–368.

The halves of the cortex of 15 day-old mouse embryos were dissected and the individual cells were obtained enzymatically (trypsin). These cells (glia and cortical neurons) are inoculated into 24-well plates. After three days (laminin-coated plates) or seven days (ornithine-coated plates), the mitosis treatment is carried out using FDU (5-fluoro-2-deoxyuridines). 15 days after the cell preparation, cell death is induced by addition of glutamate (15 minutes). After the removal of glutamate, the calpain inhibitors are added. 24 hours later, the cell damage is determined by means of the determination of lactate dehydrogenase (LDH) in the cell culture supernatant.

It is postulated that calpain also plays a part in apoptotic cell death (M. K. T. Squier et al. J. Cell. Physiol. 1994, 159, 229–237; T. Patel et al. Faseb Journal 1996, 590, 587–597). Therefore, in a further model, cell death was inducted with calcium in the presence of a calcium ionophore in a human cell line. Calpain inhibitors must pass into the cell and inhibit calpain there in order to prevent the induced cell death.

Calcium-mediated Cell Death in NT2 Cells

Cell death can be induced in the human cell line NT2 (precursor cells, Strategene GmbH) by means of calcium in the presence of the ionophore A 23187. $10^5$ cells/well were plated out into microtiter plates 20 hours before the experiment. After this period, the cells were incubated with various concentrations of inhibitors in the presence of 2.5 $\mu$M ionophore and 5 mM calcium. 0.05 ml of XTT (cell proliferation kit II, Boehringer Mannheim) was added to the reaction batch after 5 hours. The optical density is determined approximately 17 hours later, according to the instructions of the manufacturer, in the Easy Reader EAR 400 from the company SLT. The optical density at which half of the cells have died is calculated from the two controls with cells without inhibitors, which were incubated in the absence and presence of ionophore.

In a number of neurological diseases or psychological disorders, increased glutamate activity, which leads to states of overstimulation or toxic effects in the central nervous system (CNS), occurs. Glutamate mediates its effects by means of various receptors. Two of these receptors are classified by the specific agonists NMDA receptor and AMPA receptor. Substances which weaken these glutamate-induced effects can thus be employed for the treatment of these diseases, in particular for therapeutic administration against neurodegenerative diseases such as Huntington's chorea and Parkinson's disease, neurotoxic disorders after hypoxia, anoxia, ischemia and after lesions, such as occur after stroke and trauma, or alternatively as antiepileptics (cf. Arzneim. Forschung 1990, 40, 511–514; TIPS, 1990, 11, 334–338; Drugs of the Future 1989, 14, 1059–1071).

Protection Against Cerebral Overstimulation by Excitatory Amino Acids (NMDA or AMPA Antagonism in Mice)

As a result of intracerebral administration of excitatory amino acids (EAA), such a massive overstimulation is induced that in a short time this leads to spasms and to the death of the animals (mice). These symptoms can be inhibited by systemic, e.g. intraperitoneal, administration of centrally active compounds (EAA antagonists). Since the excessive activation of EAA receptors of the central nervous system plays an important part in the pathogenesis of various neurological disorders, a conclusion can be drawn from the demonstrated EAA antagonism in vivo regarding a possible therapeutic utility of the substances against CNS disorders of this type. As a measure of the efficacy of the substances, an $ED_{50}$ value was determined at which 50% of the animals become symptom-free as a result of a fixed dose of either NMDA or AMPA as a result of the prior i.p. administration of the standard substance.

It has already been shown that calpain inhibitors, too, have protective activity in cell cultures against cell death caused by EAA (H. Cauer et al., Brain Research 1993, 607, 354–356; Yu Cheg and A. Y. Sun, Neurochem. Res. 1994, 19, 1557–1564). Surprisingly, the calpain inhibitors included in this application are active even against spasms elicited in vivo (mouse) by EAA (for example NMDA or AMPA), thus pointing to a possible therapeutic use for the abovementioned CNS disorders.

The heterocyclically substituted amides I are inhibitors of cysteine derivatives such as calpain I or II and cathepsin B or L and can thus be used for the control of diseases which are associated with an increased enzyme activity of the calpain enzymes or cathepsin enzymes. The present amides I can accordingly be used for the treatment of neurodegenerative diseases which occur after ischemia, trauma, subarachnoid hemorrhages and stroke, and of neurodegenerative diseases such as multiple infarct dementia, Alzheimer's disease, Huntington's disease and of epilepsies and furthermore for the treatment of damage to the heart after cardiac ischemia, reperfusion damage after vascular occlusion, damage to the kidneys after renal ischemia, skeletal muscle damage, muscular dystrophy, damage which occurs due to proliferation of the smooth muscle cells, coronary vasospasms, cerebral vasospasms, cataracts of the eyes, restenosis of the blood vessels after angioplasty. Moreover, the amides I can be useful in the chemotherapy of tumors and metastasis thereof and for the treatment of diseases in which an increased interleukin-1 level occurs, such as in inflammations and rheumatic disorders.

In addition to the customary pharmaceutical auxiliaries, the pharmaceutical preparations according to the invention contain a therapeutically efficacious amount of the compounds I.

For local external application, for example in powders, ointments or sprays, the active compounds can be contained in the customary concentrations. As a rule, the active compounds are contained in an amount from 0.001 to 1% by weight, preferably 0.001 to 0.1% by weight.

In the case of internal administration, the preparations are administered in individual doses. 0.1 to 100 mg are provided in an individual dose per kg of body weight. The preparation can be administered daily in one or more doses depending on the nature and severity of the disorders.

According to the desired type of administration, the pharmaceutical preparations according to the invention contain the customary excipients and diluents in addition to the active compound. For local external application, pharmaceutical auxiliaries such as ethanol, isopropanol, ethoxylated castor oil, ethoxylated hydrogenated castor oil, polyacrylic acid, polyethylene glycol, polyethylene glyco stearate, ethoxylated fatty alcohols, paraffin oil, petroleum jelly and wool fat can be used. For internal administration, for example, lactose, propylene glycol, ethanol, starch, talc and polyvinylpyrrolidone are suitable.

Antioxidants such as tocopherol and butylated hydroxyanisole as well as butylated hydroxytoluene, flavor-enhancing additives, stabilizers, emulsifiers and lubricants can additionally be contained.

The substances contained in the preparation in addition to the active compound and the substances used in the production of the pharmaceutical preparations are toxicologically acceptable and compatible with the respective active compound. The pharmaceutical preparations are prepared in a customary manner, for example by mixing the active compound with other customary excipients and diluents.

The pharmaceutical preparations can be administered in various administration procedures, for example, orally, parenterally such as intravenously by infusion, subcutaneously, intraperitoneally and topically. Thus preparation forms such as tablets, emulsions, infusion and injection solutions, pastes, ointments, gels, creams, lotions, powders and sprays are possible.

EXAMPLES

Example 1

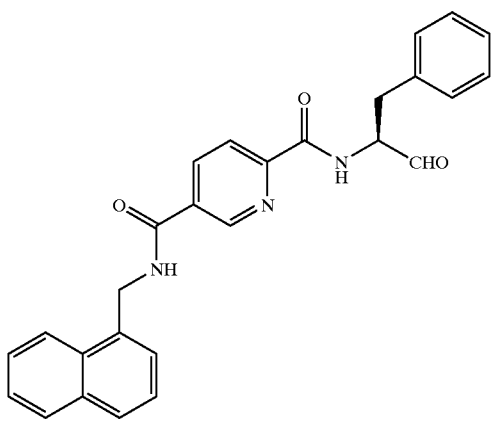

(S)-4(N-(1-Naphthylmethyl)carbamoyl)-N-(3-phenylpropan-1-al-2-yl)pyridine-2-carboxamide a) Ethyl 4-(N-(1-naphthylmethyl)carbamoyl)pyridine-2-carboxylate 4.9 g (25 mmol) of 2-ethoxycarbonylpyridine-3-carboxylic acid (N. Finch et al., J. Med. Chem. 1980, 23, 1405) were dissolved in 110 ml of tetrahydrofuran/dimethylformamide (10/1) and treated with 4.5 g (27.5 mmol) of 1,1'-carbonyldiimidazole. After the mixture had been stirred at room temperature for 30 min, 3.9 g (25 mmol) of 1-aminomethylnaphthalene were additionally added and the mixture was stirred at room temperature for a further 72 h. The tetrahydrofuran was then removed in vacuo and the residue was partitioned between 200 ml of ethyl acetate and 200 ml of aqueous sodium hydrogencarbonate solution. The organic phase was additionally washed with water, dried and concentrated in vacuo. 7.9 g (95%) of the product were obtained. 1H-NMR: [lacuna]

b) 4-(N-(1-Naphthylmethyl)carbamoyl)pyridine-2-carboxylic Acid 6.9 g (20 mmol) of the intermediate la were dissolved in 100 ml of ethanol and treated with 3.3 g (82 mmol) of sodium hydroxide, dissolved in 50 ml of water. The entire mixture was stirred at room temperature for 16 h. The reaction solution was then neutralized with 1M hydrochloric acid and the ethanol was removed in vacuo. The precipitate obtained was filtered off with suction and dried. 5.6 (89%) of the product were obtained.

c) (S)-4-(N-(1-Naphthylmethyl)carbamoyl)-N-(3-phenylpropan-1-ol-2-yl)pyridine-2-carboxamide 2.7 g (9 mmol) of the intermediate 1b and 1.4 g (9 mmol) of (S)-phenylalaninol were added to 60 ml of methylene chloride and treated with 2.3 g (22.5 mmol) of triethylamine, 50 ml of dimethylformamide and 0.4 g (3 mmol) of 1-hydroxybenzotriazole. 1.7 g (9 mmol) of 1-ethyl-3-(dimethylaminopropyl)carbodiimide hydrochloride was then added at 0° C. and the entire mixture was first stirred at 0° C. for 16 h, then at room temperature. The reaction mixture was washed successively with 100 ml of 5% strength citric acid and 100 ml of sodium hydrogencarbonate solution and, after drying, concentrated in vacuo. 2.4 g (62%) of the product were obtained.

d) (S)-4-(N-(1-Naphthylmethyl)carbamoyl)-N-(3-phenylpropan-1-al-2-yl )pyridine-2-carboxamide 1.9 g (4.4 mmol) of the intermediate compound 1c were dissolved in 50 ml of dry dimethyl sulfoxide and treated with a solution of 1.8 g (17.4 mmol) of triethylamine and 2.8 g (17.4 mmol) of pyridine-sulfur trioxide complex in 50 ml of dry dimethyl sulfoxide. The entire mixture was stirred at room temperature for 16 h. The reaction mixture was then added to water and the precipitate was filtered off with suction. 1.5 g (80%) of the product were obtained.

1H-NMR ($D_6$-DMSO): δ=3.1 (1H), 3.5(1H), 4.7(1H), 5.1 (1H), 7.1–7.3(6H), 7.4–7.7(5H), 7.9(1H), 7.95(1H), 8.15 (1H), 8.2(1H), 8.4(1H), 9.1(1H), 9.2(1H), 9.4(1H) and 9.8 (1H) ppm.

Example 2

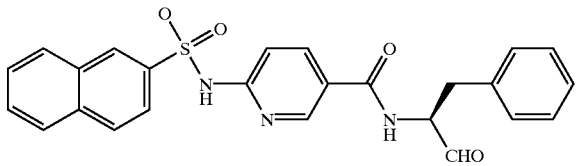

(S)-2-(2-Naphthalenesulfonamido)-N-(3-phenylpropan-1-al-2-yl)-pyridine-3-carboxamide a) Methyl 2-(2-naphthalenesulfonamido)pyridine-3-carboxylate 5.9 g (26 mmol) of naphthalene-2-sulfonyl chloride were added in portions at room temperature to 4.7 g (25 mmol) of methyl 6-aminonicotinate hydrochloride in 100 ml of dry pyridine. The entire mixture was then stirred at room temperature for 16 h. The reaction solution was then poured onto 500 ml of water and the precipitate obtained was filtered off with suction. 6.4 g (75%) of the product were obtained.

b) 2-(2-Naphthalenesulfonamido)pyridine-3-carboxylic Acid 6 g (17 mmol) of the intermediate compound 2a, dissolved in 100 ml of methanol, were stirred at room temperature for 16 h with 4.2 g (104 mmol) of sodium hydroxide, dissolved in 100 ml of water. The organic solvent was then removed in vacuo and the aqueous solution obtained was neutralized with 1M hydrochloric acid. The resulting precipitate was filtered off with suction. 5.1 g (90%) of the product were obtained.

c) (S)-2-(2-Naphthalenesulfonamido)-N-(3-phenylpropan-1-ol-2-yl)-pyridine-3-carboxamide 2.5 g (7.5 mmol) of the intermediate compound 2b was reacted with (S)-phenylalaninol analogously to procedure 1c. 0.7 g (21%) of the product was obtained.

d) (S)-2-(2-Naphthalenesulfonamido)-N-(3-phenylpropan-1-al-2-yl)-pyridine-3-carboxamide 0.5 g (1.2 mmol) of the intermediate compound 2c were oxidized analogously to the procedure 1d, 0.4 g (78%) of the product being obtained.

1H-NMR ($D_6$-DMSO): δ=2.8(1H), 3.3(1H), 4.5(1H), 7.0–7.4 (5H), 7.7(2H), 7.9(1H), 8.1(3H), 8.25(1H), 8.5(1H), 8.7 (1H), 8.9(1H), 9.6(1H) and about 12.5(broad, 1H) ppm.

Example 3

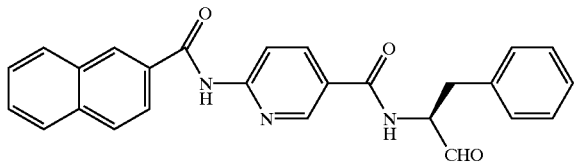

(S)-2-(2-Naphthalenamido)-N-(3-phenylpropan-1-al-2-yl)-pyridine-5-carboxamide a) 6-Aminonicotinic Acid Hydrochloride 20 g (0.145 mol) of 6-aminonicotinic acid were refluxed for approximately 5 h in a mixture of 200 ml of methanol [lacuna] 250 ml of 2.5 M hydrochloric acid. The entire mixture was then concentrated in vacuo and 26.6 g (97%) of the product were obtained.

30 b) Methyl 6-(2-naphthalenamido)nicotinate 4.7 g (25 mmol) of the intermediate compound 3a were dissolved in 100 ml of pyridine and treated in portions at room temperature with 5 g (25 mol ) of 2-naphthoyl chloride. The entire mixture was stirred at room temperature for 16 h. The reaction mixture was then poured onto water and the precipitate obtained was filtered off with suction. 5.4 g (70%) of the product were obtained.

c) 6-(2-Naphthalenamido)nicotinic Acid 4.7 g (15 mmol) of the intermediate compound 3b were dissolved in 75 ml of ethanol and treated with 2.5 g of sodium hydroxide, dissolved in 50 ml of water. The entire mixture was stirred at room temperature for 16 h. The ethanol was then removed in vacuo and the aqueous residue was neutralized with 1M hydrochloric acid. The precipitate obtained was filtered off with suction. 3.1 g (69%) of the product were obtained.

d) (S)-2-(2-Naphthalenamido)-N-(3-phenylpropan-1-ol-2-yl)-pyridine-5-carboxamide 2.7 g (9.2 mmol) of the intermediate compound 3c were reacted with (S)-phenylalaninol analogously to the procedure 1c. 2.1 g (54%) of the product were obtained.

e) (S)-2-(2-Naphthalenamido)-N-(3-phenylpropan-1-al-2-yl)-pyridine-5-carboxamide 1.7 g (4 mmol) of the intermediate compound 3d were oxidized analogously to the procedure 1d. 1.3 g (79%) of the product were obtained.

MS: m/e=423 ($M^+$).

Example 4

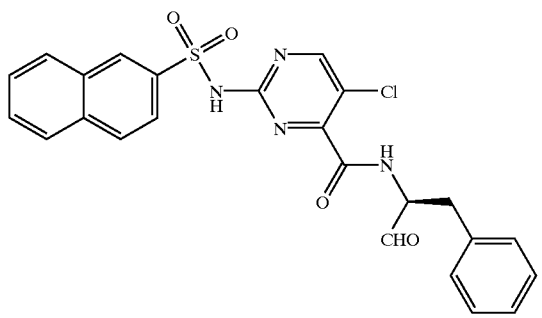

(S)-5-Chloro-2-(2-naphthalenesulfonamido)-N-(3-phenylpropan-1-al-2-yl)pyrimidine-6-carboxamide a) Ethyl 5-(chloro-2-(2-naphthalenesulfonamido) pyrimidine-6-carboxylate 6 g (26 mmol) of 2-naphthalenesulfonyl chloride were added at room temperature to 5 g (25 mmol) of ethyl 2-amino-5-chloropyrimidine-6-carboxylate in 100 ml of dry pyridine. The entire mixture was additionally stirred for 16 h. The batch was then poured onto water and the precipitate obtained was filtered off with suction. 9.8 g (59%) of the product were obtained.

b) 5-Chloro-2-(2-naphthalenesulfonamido)pyrimidine-6-carboxylic Acid 5.6 g (14 mmol) of the intermediate compound 4a were dissolved in 100 ml of methanol/tetrahydrofuran (1/1) and hydrolyzed at room temperature with 2.8 g of sodium hydroxide, dissolved in 10 ml of water. After 16 h, the organic solvent was removed in vacuo and the aqueous phase was adjusted to pH=6 using 2M hydrochloric acid. The precipitate formed was filtered off with suction. 2.8 g (55%) of the product were obtained.

c) (S)-5-Chloro-2-(2-naphthalenesulfonamido)-N-(3-phenylpropan-1-ol-2-yl)pyrimidine-6-carboxamide 1.9 g (5.2 mmol) of the intermediate compound 4b were reacted with (S)-phenylalaninol analogously to procedure 1c. 1.4 g (55%) of the product were obtained.

d) (S)-5-Chloro-2-(2-naphthalenesulfonamido)-N-(3-phenylpropan-1-al-2-yl)pyrimidine-6-carboxamide 1.73 [lacuna] (2.5 mmol) of the intermediate compound 4c were oxidized analogously to procedure 1d. 1.1 g (85%) of the product were obtained.

1H-NMR (D$_6$-DMSO): δ=2.95(1H), 3.4(1H), 4.6(1H), 7.2–8.2 (12H) 8.45(1H), 9.2(1H) and 9.7(1H) ppm Example 5

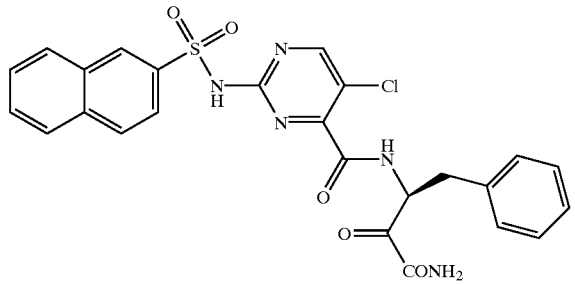

(S)-5-Chloro-2-(2-naphthalenesulfonamido)-N-(1-carbamoyl-1-oxo-3-phenylpropan-2-yl)pyrimidine-6-carboxamide a) (S)-5-Chloro-2-(2-naphthalenesulfonamido)-N-(1-carbamoyl-1-hydroxy-3-phenylpropan-2-yl)pyrimidine-6-carboxamide 0.77 g (2.1 mmol) of the intermediate compound 4b and (2S),(3R,S)-3-amino-2-hydroxy-3-phenylbutyramide was reacted analogously to procedure 1c. 0.24 g (23%) of the product was obtained.

b) (S)-5-Chloro-2-(2-naphthalenesulfonamido)-N-(1-carbamoyl-1-oxo-3-phenylpropan-2-yl)pyrimidine-6-carboxamide 0.19 g (0.35 mmol) of the intermediate compound 5a was oxidized analogously to procedure 1d. 0.024 g of the product was obtained.

1H-NMR (D$_6$-DMSO): δ=3.0(1H), 3.25(1H), 5.4(1H), 7.2–8.0 (11H), 8.1(1H), 8.4(1H), 9.0(1H).

Example 6

(S)-2-(2-Naphthalenamido)-N-(3-phenylpropan-1-al-2-yl)-thiazole-4-carboxamide

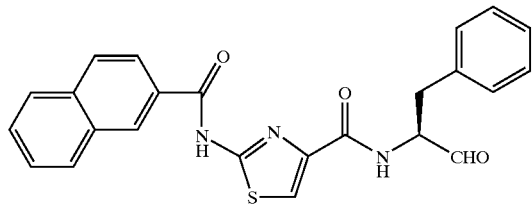

a) Ethyl 2-(2-naphthalenamido)thiazole-4-carboxylate 4.7 g (24.9 mmol) of 2-naphthoyl chloride, dissolved in 50 ml of anhydrous tetrahydrofuran, were added dropwise at 0° C. to 4 g (23.3 mmol) of ethyl 2-aminothiazole-4-carboxylate and 6.4 ml (46.5 mmol) of triethylamine in 150 ml of anhydrous tetrahydrofuran. The entire mixture was then stirred for 16 h. The reaction solution was then poured into plenty of water and extracted with ethyl acetate. The organic phase was then washed with aqueous sodium hydrogencarbonate solution, dried and concentrated in vacuo. The residue was purified by chromatography (eluent: methylene chloride), 5.6 g (82%) of the product being obtained.

b) 2-(2-Naphthalenamido)thiazole-4-carboxylic Acid 5.4 g (16.6 mmol) of the intermediate compound 6a were dissolved in 50 ml of tetrahydrofuran and treated with 100 ml of 2M sodium hydroxide solution. The entire mixture was stirred at room temperature for 16 h. The batch was then diluted with water and neutralized with concentrated acetic acid. The precipitate formed was filtered off with suction. 4.7 g (95%) of the product were obtained.

(S)-2-(2-Naphthalenamido)-N-(3-phenylpropan-1-ol-2-yl)-thiazole-4-carboxamide 1 g (3.4 mmol) of the intermediate compound 6b and and (2S),(3R,S)-3-amino-2-hydroxy-3-phenylbutyramide were reacted analogously to procedure 1c. 1.2 g (93%) of the product were obtained.

(S)-2-(2-Naphthalenamido)-N-(3-phenylpropan-1-al-2-yl)-thiazole-4-carboxamide 1 g (2.3 mmol) of the intermediate compound 6c were oxidized analogously to procedure 1d. 0.73 g (74%) of the product was obtained.

MS: m/e=429 (M$^+$).

Example 7

(S)-2-(2-Naphthalenamido)-N-(1-carbamoyl-1-oxo-3-phenylpropan-2-yl)thiazole-4-carboxamide

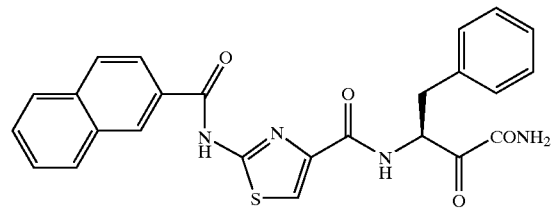

a) (S)-2-(2-Naphthalenamido)-N-(1-carbamoyl-1-hydroxy-3-phenyl-propan-2-yl)thiazole-4-carboxamide 1.35 g (4.5 mmol) of the intermediate compound 6b and 1.4 g of (2S)(3R,S)-3-amino-2-hydroxy-3-phenylbutyramide trifluoroacetate were reacted analogously to procedure 1c. 1.4 g (66%) of the product were obtained.

b) (S)-2-(2-Naphthalenamido)-N-(1-carbamoyl-1-oxo-3-phenylpropan-2-yl)thiazole-4-carboxamide 1.2 g (2.5 mmol) of the intermediate compound 7a were oxidized analogously to procedure 1d. 1.05 g (88%) of the product were obtained.

MS: m/e=472 (M$^+$).

Example 8

(S)-N-(1-Carbamoyl-1-oxo-3-phenylpropan-2-yl)-4-methyl-1-(2-naphthalenemethyl)imidazole-5-carboxamide

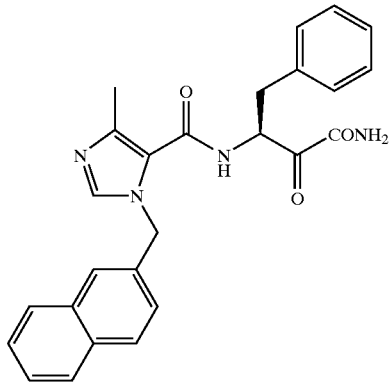

a) Ethyl 4-methyl-1-(2-naphthalenemethyl)imidazole-5-carboxylate 4.2 g (27.2 mmol) of etheyl 4-methylimidazole-5-carboxylate, 3.8 g (27.2 mmol) of potassium carbonate and 6.0 (27.2 mmol) of 2-bromomethylnaphthalene were heated at 100° C. for 1 h in 100 ml of dimethylformamide. The entire mixture was then poured onto water and extracted with ethyl acetate. The organic phase was dried and concentrated in vacuo. The residue was then purified by chromatography on silica gel (eluent: ethyl acetate). 4.8 g (60%) of the product were obtained.

b) 4-Methyl-1-(2-naphthalenemethyl)imidazole-5-carboxylic Acid 4.6 g (15.6 mmol) of the intermediate compound 8a were dissolved in 50 ml of tetrahydrofuran, treated with 100 ml of 1M sodium hydroxide solution and the entire mixture was then refluxed for 6 h. The organic solvent was then removed in vacuo and the aqueous residue was neutralized with acetic acid. The precipitate formed was filtered off with suction. 3.5 g (85%) of the product were obtained.

c) (S)-N-(1-Carbamoyl-1-hydroxy-3-phenylpropan-2-yl)-4-methyl-1-(2-naphthalenemethyl)imidazole-5-carboxamide 1 g (3.8 mmol) of the intermediate compound 8b and and 1.2 g (3.8 mmol) of (2S),(3R,S)-3-amino-2-hydroxy-3-phenylbutyramide trifluoroacetate were reacted analogously to procedure 1c. 0.7 g (42%) of the product was obtained.

d) (S)-N-(1-Carbamoyl-1-oxo-3-phenylpropan-2-yl)-4-methyl-1-(2-naphthalenemethyl)-imidazole-5-carboxamide 0.6 g (1.4 mmol) of the intermediate compound 8c was oxidized analogously to procedure 1d. 0.33 g (56%) of the product was obtained.

MS: m/e=440 (M⁺).

Example 9

(S)-N-(1-Carbamoyl-1-oxo-3-phenylpropan-2-yl)-2-methyl-1-(2-naphthylmethyl)imidazole-5-carboxamide

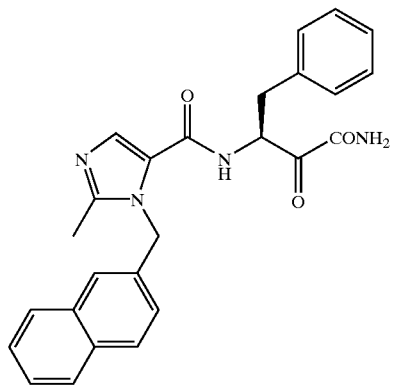

a) Ethyl 2-methyl-1-(2-naphthyl)methylimidazole-4-carboxylate 4.6 g (29.8 mmol) of ethyl 2-methylimidazole-4-carboxylate and 6.6 g (29.8 mmol) of 2-bromomethylnaphthalene were reacted analogously to procedure 8a. 5.7 g (65%) of the product were obtained.

b) 2-Methyl-1-(2-naphthyl)methylimidazole-4-carboxylic Acid 0 5.5 g (18.7 mmol) of the intermediate compound 9a were hydrolyzed analogously to procedure 8b. 3.2 g (65%) of the product were obtained.

c) (S)-N-(1-Carbamoyl-1-hydroxy-3-phenylpropan-2-yl)-2-methyl-1-(2-naphthylmethyl)imidazole-5-carboxamide 1 g (3.8 mmol) of the intermediate compound 9b and and 1.2 g (3.8 mmol) of (2S),(3R,S)-3-amino-2-hydroxy-3-phenylbutyramide trifluoroacetate were reacted analogously to procedure 1c. 0.65 g (39%) of the product was obtained.

d) (S)-N-(1-Carbamoyl-1-oxo-3-phenylpropan-2-yl)-2-methyl-1-(2-naphthylmethyl)imidazole-5-carboxamide 0.6 g (1.4 mmol) of the intermediate product 9c was oxidized analogously to procedure 1d. 0.42 g (71%) of the product was obtained.

MS: m/e=440 (M⁺).

Example 10

(S)-N-(1-Carbamoyl-1-oxo-3-phenylpropan-2-yl)-1-(2-naphthyl-methyl)imidazole-2-carboxamide

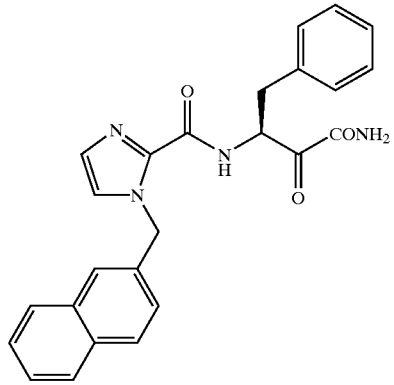

a) Butyl 1-(2-naphthyl)methylimidazole-2-carboxylate 5.0 g (29.7 mmol) of butyl imidazole-2-carboxylate and 6.6 g (29.7 mmol) of 2-bromomethylnaphthalene were reacted analogously to procedure 8a. 6.4 g (71%) of the product were obtained.

b) 1-(2-Naphthyl)methylimidazole-2-carboxylic Acid 6.2 g (20.1 mmol) of the intermediate compound 10a were hydrolyzed analogously to procedure 8b. 4.2 g (83%) of the product were obtained.

c) (S)-N-(1-Carbamoyl-1-hydroxy-3-phenylpropan-2-yl)-1-(2-naphthylmethyl)imidazole-2-carboxamide 1.1 g (4.4 mmol) of the intermediate compound 10b and and 1.3 g (4.4 mmol) of (2S),(3R,S)-3-amino-2-hydroxy-3-phenylbutyramide trifluoroacetate were reacted analogously to procedure 1c. 1.3 g (70%) of the product were obtained.

d) (S)-N-(1-Carbamoyl-1-oxo-3-phenylpropan-2-yl)-1-(2-naphthyl-methyl)imidazole-2-carboxamide 1.0 g (2.3 mmol) of the intermediate compound 10c were oxidized analogously to procedure 1d. 0.73 g (74%) of the product was obtained.

MS: m/e=426 (M+).

Example 11

(S)-1-Benzyl-N-(1-carbamoyl-1-oxo-3-phenylpropan-2-yl)-imidazole-2-carboxamide

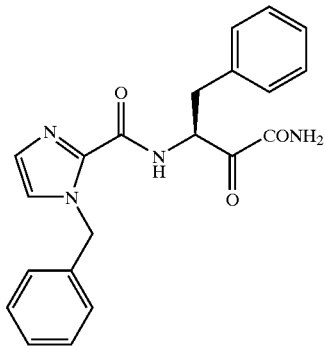

a) Butyl 1-benzylimidazole-2-carboxylate 5.4 g (32.1 mmol) of butyl imidazole-2-carboxylate were reacted with 4.1 g (32.1 mmol) of benzyl chloride analogously to procedure 8a. 7.3 g (78%) of the product were obtained.

b) 1-Benzylimidazole-2-carboxylic Acid 7 g (27.1 mmol) of the intermediate compound 11a were hydrolyzed using sodium hydroxide solution analogously to procedure 8b. 3.7 g (68%) of the product were obtained.

c) (S)-1-Benzyl-(1-carbamoyl-1-hydroxy-3-phenylpropan-2-yl)-imidazole-2-carboxamide 1.0 g (5.1 mmol) of the intermediate compound 11b and and 1.6 g (5.1 mmol) of (2S),(3R,S)-3-amino-2-hydroxy-3-phenylbutyramide trifluoroacetate were reacted analogously to procedure 1c. 1.1 g (58%) of the product were obtained.

d) (S)-1-Benzyl-N-(1-carbamoyl-1-oxo-3-phenylpropan-2-yl)-imidazole-2-carboxamide 1.0 g (2.3 mmol) of the intermediate compound 11c were oxidized analogously to procedure 1d. 0.79 g (80%) of the product was obtained.

MS: m/e=376 (M+).

Example 12

(S)-N-(1-Carbamoyl-1-oxo-3-phenylpropan-2-yl)-1-(2-naphthylmethyl)imidazole-5-carboxamide

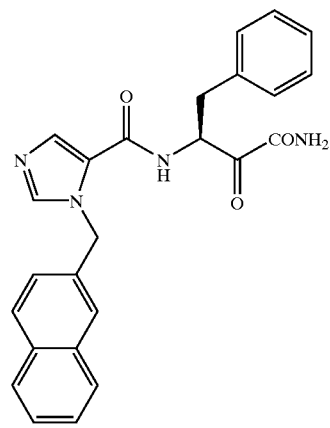

a) Ethyl 1-(2-naphthylmethyl)imidazole-5-carboxylate 2.4 g (17.1 mmol) of butyl imidazole-5-carboxylate were reacted with 4.1 g (32.1 mmol) of benzyl chloride analogously to procedure 8a. 7.3 g (78%) of the product were obtained.

b) -1(2-Naphthylmethyl)imidazole-5-carboxylic Acid 3 g (10.7 mmol) of the intermediate compound 12a were hydrolyzed using sodium hydroxide solution analogously to procedure 8b. 1.9 g (73%) of the product were obtained.

c) (S)-N-(1-Carbamoyl-1-hydroxy-3-phenylpropan-2-yl)-1-(2-naphthylmethyl) imidazole-5-carboxamide 1.0 g (4.0 mmol) of the intermediate compound 12b and 1.2 g (4.0 mmol) of (2S),(3R,S)-3-amino-2-hydroxy-3-phenylbutyramide trifluoroacetate were reacted analogously to procedure 1c. 0.85 g (51%) of the product was obtained.

d) (S)-N-(1-Carbamoyl-1-oxo-3-phenylpropan-2-yl)-1-(2-naphthyl-methyl)imidazole-5-carboxamide 0.8 g (1.9 mmol) of the intermediate compound 12c was oxidized analogously to procedure 1d. 0.41 g (52%) of the product was obtained.

MS: m/e=426 (M+).

Example 13

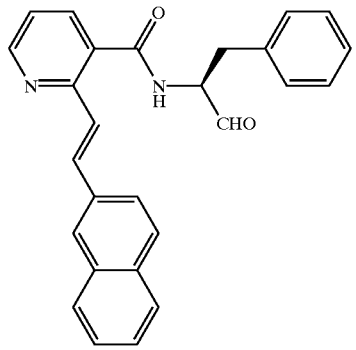

(S)-2-(2-Naphthyl)ethen-1-yl)-N-(3-phenylpropan-1-al-2-yl)-pyridine-3-carboxamide a) Ethyl 2-(2-naphthylethen-1-yl)pyridine-3-carboxylate Hydrochloride 10 g (43.5 mmol) of ethyl 2-bromopyridine-3-carboxylate, 8.7 g (56.5 mmol) of 2-vinylnaphthalene, 15 ml (0.11 mol) of triethylamine, 0.36 g of palladium(II) acetate and 0.96 g of tri-o-tolylphosphine were dissolved in 150 ml of dimethylformamide. A further 1 ml of water was then added and the entire mixture was refluxed for 3 h. The entire mixture was then extracted with ether. The organic phase was additionally washed with water, dried and concentrated in vacuo. The residue was dissolved in acetone and treated with hydrogen chloride, dissolved in dioxane. The product was then precipitated by addition of ether. 8.7 g (67%) of the product were obtained.

b) 2-(2-Naphthylethen-1-yl)pyridine-3-carboxylic Acid 8.5 g (28 mmol) of the intermediate product 13a were dissolved in 70 ml of tetrahydrofuran and treated with 140 ml of 2M sodium hydroxide solution. The entire mixture was refluxed for 8 h. The batch was then poured onto ice water and neutralized with acetic acid. The slowly crystallizing product was filtered off with suction and dried. 5.6 g (73%) of the product were obtained.

c) (S)-2-(2-Naphthyl)ethen-1-yl-N-(3-phenylpropan-1-ol-2-yl)pyridine-3-carboxamide 2 g (7.3 mmol) of the intermediate 13b and 1.1 g (7.3 mmol) of (2S),(3R,S)-3-amino-2-hydroxy-3-phenylbutyramide trifluoroacetate were reacted analogously to procedure 1c. 2.1 g (71%) of the product were obtained.

d) (S)-2-(2-Naphthyl)ethen-1-yl)-N-(3-phenylpropan-1-al-2-yl)pyridine-3-carboxamide 1.9 g (4.7 mmol) of the intermediate compound 13c were oxidized analogously to procedure 1d. 0.56 g (30%) of the product was obtained.

MS: m/e=406 (M+).

Example 14

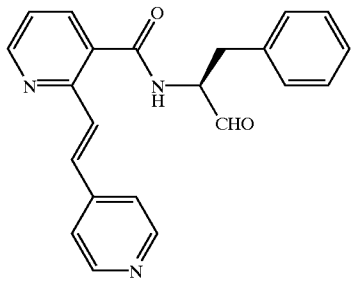

(S)-N-(3-Phenylpropan-1-al-2-yl)-2-(4-pyridyl)ethen-1-yl)-pyridine-3-carboxamide a) Ethyl 2-(4-pyridine)ethen-1-ylpyridine-3-carboxylate 11.5 g (49.9 mmol) of ethyl 2-bromopyridine-3-carboxylate and 6.8 g (64.9 mmol) of 4-vinylpyridine were reacted analogously to procedure 13a. 7.0 g (49%) of the product were obtained.

b) 2-(4-Pyridyl)ethen-1-ylpyridine-3-carboxylic acid 7.0 g (27.5 mmol) of the intermediate 14a were dissolved in 50 ml of tetrahydrofuran and treated with 100 ml of 2M sodium hydroxide solution. The entire mixture was refluxed for 2 h. The organic solvent was then removed in vacuo and the aqueous phase obtained was acidified with acetic acid. The aqueous phase was concentrated and the residue was purified by chromatography (eluent: ethyl acetate/methanol/acetic acid=50/50/1)d. 5.5 g (89%) of the product were obtained.

c) (S)-N-(3-Phenylpropan-1-ol-2-yl)-2-(4-pyridyl)ethen-1-ylpyridine-3-carboxamide 1.5 g (6.6 mmol) of the intermediate 14b and 1.0 g (6.6 mmol) of (S)-2-amino-3-phenylpropanol were reacted analogously to procedure 1c. 1.7 g (72%) of the product were obtained.

d) (S)-N-(3-Phenylpropan-1-al-2-yl)-2-(4-pyridyl)ethen-1-ylpyridine-3-carboxamide 1.5 g (4.2 mmol) of the intermediate compound 14c were oxidized analogously to procedure 1d. 0.71 g (48%) of the product was obtained.

MS: m/e=357 (M+).

The following examples were prepared analogously to the above examples and procedures:

Example 15

(S)-N-(3-Phenylpropan-1-al-2-yl)-2-(4-pyridyl)quinoline-4-carboxamide $^1$H-NMR (d$_6$-DMSO): δ=3.0(1H), 3.4(1H), 4.8(1H), 7.25 (1H), 7.7(2H), 7.9(2H), 8.1(1H9, 8.25(1H), 8.7(1H), 9.0 (1H9, 9.5(1H) and 9.8(1H) ppm.

Example 16

(S)-N-(3-Phenylpropan-1-al-2-yl)-2-(2-pyridyl)quinoline-4-carboxamide $^1$H-NMR (D$_6$-DMSO): δ=2.9(1H), 3.3(1H9, 4.8(1H), 7.2-(.2(11H), 8.5(1H), 8.6(1H), 8.8(1H), 9.4(1H) and 9.0(1H) ppm.

Example 17

N-(1-Carbamoyl-oxo-3-phenylpropan-2-yl)-2-(2-pyridyl)quinoline-4-carboxamide

MS: m/e=424 (M+).

Example 18

N-(1-Carbamoyl-1-oxo-3-phenylpropan-2-yl)-2-(E-2-(4-pyridyl)-ethen-1-yl)pyridine-3-carboxamide $^1$H-NMR (CF$_3$COOD): δ=3.1(1H), 3.7(1H), 6.1(1H), 7.1–7.6 (5H), 8.0(1H), 8.1–8.5(4H9, 8.6(1H), 9.0(2H) and 9.1(1H) ppm.

Example 19

N-(1-Carbamoyl-1-oxo-3-phenylpropan-2-yl)-2-(2-pyridyl)-quinoline-4-carboxamide

MS: m/e =424 (M+).

Example 20

N-(1-Carbamoyl-1-oxo-3-phenylpropan-2-yl)-2-(1,2,3,4-tetrahydro-ixoquinolin-2-yl)pyridine-3-carboxamide $^1$H-NMR (D$_6$-DMSO): δ=2.8(2H), 2.9(1H), 3.2(2H), 3.3 (1H), 4.3(1H), 5.3(1H), 6.8(1H), 7.0–7.5 (9H), 7.5(1H), 7.9–8.1 (2H) and 9.0(1H) ppm.

Example 21

N-(1-Carbamoyl-1-oxo-3-phenylpropan-2-yl)-2-(6,7-dimethoxy-1,2,3,4-tetrahydroisoquinolin-2-yl)pyridine-3-carboxamide $^1$H-NMR (D$_6$-DMSO): δ=2.7(2H), 2.8(1H), 3.2(2H), 3.4 (1H), 3.7(1H), 4.2(1H), 5.3(1H9, 6.7(1H), 6.95(1H), 7.1–7.5 (6&H) 7.9(1H), 8.1(1H), 8.4(1H), 9.0(1H) ppm.

Example 22

N-(1-Carbamoyl-1-oxo-3-phenylpropan-2-yl)-2-(3-phenylpyrrolidin-1-yl)pyridine-3-carboxamide $^1$H-NMR (CF$_3$COOD): δ=2.0–2.7(2H), 2.95(1H), 3.3–4.0 (6H), 5.9(1H), 6.9(1H), 7.0–7.5(10H) and 7.9(1H) ppm.

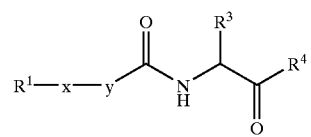

| Example | R¹ | X | Y | R³ | R⁴ |
|---|---|---|---|---|---|
| 15 | 4-pyridyl | -CH=CH- | 2-methyl-3-pyridyl | CH₂Ph | CONH₂ |
| 16 | 4-pyridyl | -CH=CH- | 2-methyl-3-pyridyl | CH₂Ph | CONH(CH₂)₃-pyridinium |
| 17 | 4-pyridyl | -CH=CH- | 2-methyl-3-pyridyl | CH₂Ph | CONH(CH₂)₃N(Et)₂ |
| 18 | 4-pyridyl | -CH=CH- | 2-methyl-3-pyridyl | CH₂Ph | CONH(CH₂)₃Ph |
| 19 | 4-pyridyl | -CH=CH- | 2-methyl-3-pyridyl | (CH₂)₃—CH₃ | CONH₂ |
| 20 | 4-pyridyl | -CH=CH- | 2-methyl-3-pyridyl | (CH₂)₃—CH₃ | H |
| 21 | 2-pyridyl | -CH=CH- | 2-methyl-3-pyridyl | CH₂Ph | H |
| 22 | 2-pyridyl | -CH=CH- | 2-methyl-3-pyridyl | CH₂Ph | CONH₂ |
| 23 | 2-pyridyl | -CH=CH- | 2-methyl-3-pyridyl | (CH₂)₃—CH₃ | CONH₂ |
| 24 | 2-pyridyl | -CH=CH- | 2-methyl-3-pyridyl | (CH₂)₃—CH₃ | H |

-continued $$R^1-X-Y-\underset{H}{N}-\overset{O}{\underset{\|}{C}}-\underset{\underset{O}{\|}}{\overset{R^3}{C}}-R^4$$

| Example | R¹ | X | Y | R³ | R⁴ |
|---|---|---|---|---|---|
| 25 | 2-pyridyl |  | 2-methyl-3-pyridyl | CH₂Ph | H |
| 26 | 2-pyridyl |  | 2-methyl-3-pyridyl | CH₂Ph | CONH₂ |
| 27 | 4-pyridyl |  | 2-methyl-3-pyridyl | CH₂Ph | CONH₂ |
| 28 | 4-pyridyl |  | 2-methyl-3-pyridyl | CH₂Ph | H |
| 29 | 3-pyridyl |  | 2-methyl-3-pyridyl | CH₂Ph | H |
| 30 | 3-pyridyl |  | 2-methyl-3-pyridyl | CH₂Ph | CONH₂ |
| 31 | phenyl | -CH=CH- | 2-methyl-3-pyridyl | CH₂Ph | H |
| 32 | phenyl | -CH=CH- | 2-methyl-3-pyridyl | CH₂Ph | CONH₂ |
| 33 | phenyl | -CH=CH- | 2-methyl-3-pyridyl | (CH₂)₃CH₃ | H |
| 34 | phenyl | -CH=CH- | 2-methyl-3-pyridyl | (CH₂)₃CH₃ | CONH₂ |

-continued $$R^1-X-Y-\underset{H}{N}-\underset{\underset{O}{\|}}{\overset{\overset{O}{\|}}{C}}-\underset{R^3}{\overset{|}{C}}H-\underset{O}{\overset{\|}{C}}-R^4$$

| Example | R¹ | X | Y | R³ | R⁴ |
|---|---|---|---|---|---|
| 35 | phenyl | -CH=CH-CH₂- | 2,3-dimethylpyridin-yl | CH₂Ph | CONH-(CH₂)₃-morpholino |
| 36 | phenyl | -CH=CH-CH₂- | 2,3-dimethylpyridin-yl | | CONH-(CH₂)₃-N-pyridinium |
| 37 | phenyl | -CH=CH-CH₂- | 2,3-dimethylpyridin-yl | CH₂Ph | |
| 38 | phenyl | -CH=CH-CH₂- | 2,3-dimethylpyridin-yl | CH₂Ph | CONH-(CH₂)₃-N-pyridinium |
| 39 | phenyl | -CH=CH-CH₂- | 2,3-dimethylpyridin-yl | CH₂Ph | CONH-(CH₂)₃-N(Et)₂ |
| 40 | phenyl | -CH=CH-CH₂- | 2,3-dimethylpyridin-yl | CH₂Ph | CONH-(CH₂)₃-(2-pyridyl) |
| 41 | 3,4-dimethoxyphenyl | -CH=CH-CH₂- | 2,3-dimethylpyridin-yl | CH₂Ph | H |
| 42 | 3,4-dimethoxyphenyl | -CH=CH-CH₂- | 2,3-dimethylpyridin-yl | CH₂Ph | CONH₂ |
| 43 | 2-naphthyl | —SO₂NH— | 2-methylpyridin-5-yl | CH₂Ph | H |
| 44 | 2-naphthyl | —SO₂NH— | 2-methylpyridin-5-yl | CH₂Ph | CONH₂ |

-continued
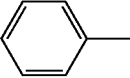
| Example | R$^1$ | X | Y | R$^3$ | R$^4$ |
|---|---|---|---|---|---|
| 45 | 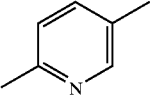 | —SO$_2$NH— | 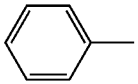 | CH$_2$Ph | H |
| 46 | 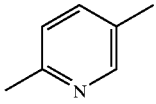 | —SO$_2$NH— | 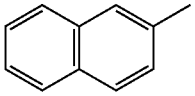 | CH$_2$Ph | CONH$_2$ |
| 47 | 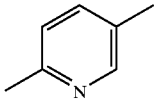 | —CONH— | 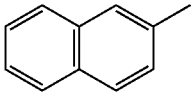 | CH$_2$Ph | H |
| 48 | 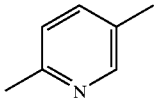 | —CONH— | 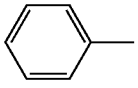 | CH$_2$Ph | CONH$_2$ |
| 49 | 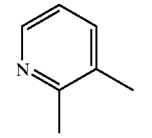 | ≡ | 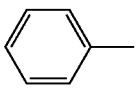 | CH$_2$Ph | H |
| 50 | 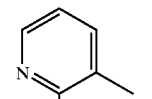 | ≡ | 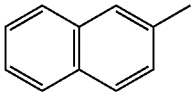 | CH$_2$Ph | CONH$_2$ |
| 51 | 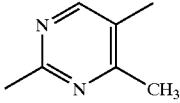 | —SO$_2$NH— | 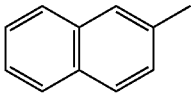 | CH$_2$Ph | H |
| 52 | 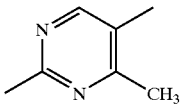 | —SO$_2$NH— | 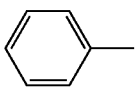 | CH$_2$Ph | CONH$_2$ |
| 53 | 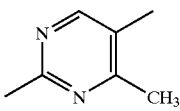 | —SO$_2$NH— | 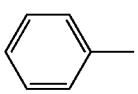 | CH$_2$Ph | CONH$_2$ |
| 54 | 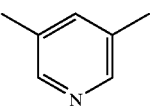 | —NHCO— | 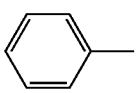 | CH$_2$Ph | H |
| 55 | 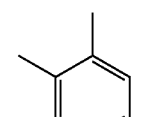 | —NHCO— | | CH$_2$Ph | CONH$_2$ |

-continued
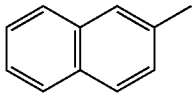
| Example | R¹ | X | Y | R³ | R⁴ |
|---|---|---|---|---|---|
| 56 | 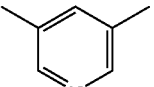 | —NHCO— | 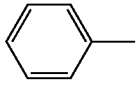 | CH₂Ph | CONH₂ |
| 57 | 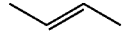 | 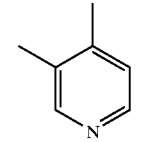 | 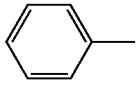 | CH₂Ph | H |
| 58 | 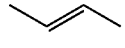 | 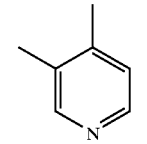 | 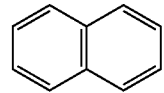 | CH₂Ph | CONH₂ |
| 59 | 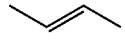 | 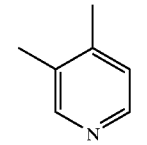 | 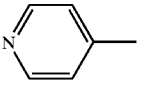 | CH₂Ph | CONH₂ |
| 60 | 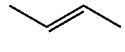 | 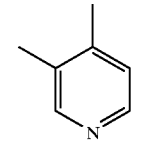 | 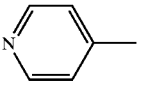 | CH₂Ph | CONH₂ |
| 61 | 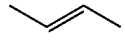 | 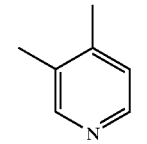 | 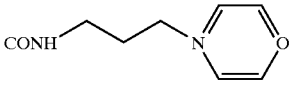 | CH₂Ph | 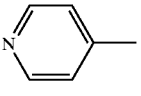 |
| 62 | 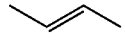 | 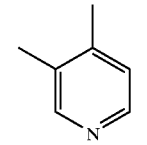 | 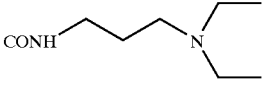 | CH₂Ph | 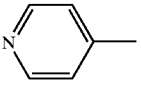 |
| 63 | 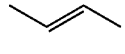 | 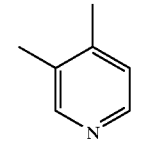 | 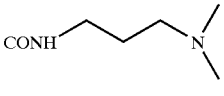 | CH₂Ph | 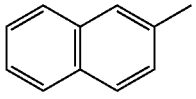 |
| 64 | 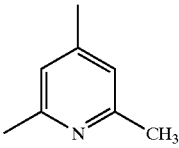 | —SO₂NH— | (2,6-dimethylpyridin-4-yl) | CH₂Ph | CONH₂ |

-continued
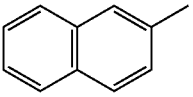
| Example | R¹ | X | Y | R³ | R⁴ |
|---|---|---|---|---|---|
| 65 | 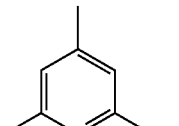 | —SO₂NH— | 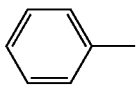 | CH₂Ph | H |
| 66 | 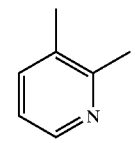 | —CH₂O— | 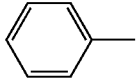 | CH₂Ph | H |
| 67 | 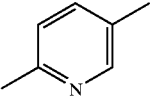 | —CH₂O— | 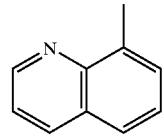 | CH₂Ph | CONH₂ |
| 68 | 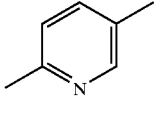 | —SO₂NH— | 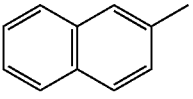 | CH₂Ph | CONH₂ |
| 69 | 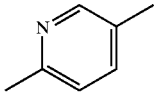 | —NHCO— | 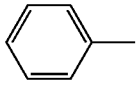 | CH₂Ph | H |
| 70 | 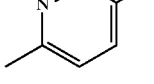 | —CH₂NHCO— | 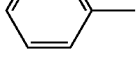 | CH₂Ph | CONH₂ |
| 71 | 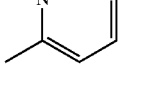 | —SO₂NH— | 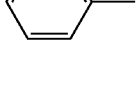 | CH₂Ph | |
| 72 | 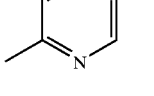 | —SO₂NH— | 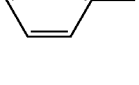 | CH₂Ph | 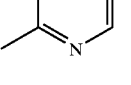 |
| 73 | 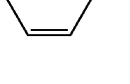 | —SO₂NH— | 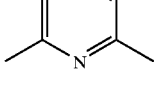 | CH₂Ph | 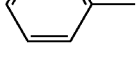 |
| 74 | 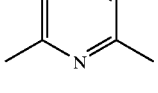 | —SONH₂—  |  | CH₂Ph | CONH₂ |
| 75 |  | —SONH₂—  |  | CH₂Ph |  |

-continued

| Example | R¹ | X | Y | R³ | R⁴ |
|---------|-----|-----|-----|-----|-----|
| 76 | phenyl | —SONH₂— phenyl | 2,6-pyridinyl | CH₂Ph | CONH(CH₂)₃N(CH₃)₂ |
| 77 | 2-naphthyl | —SO₂NH— | 2,6-pyridinyl | CH₂Ph | CONH₂ |
| 78 | 2-naphthyl | —CH₂CH₂ | 2,3-pyridinyl | CH₂Ph | CONH₂ |
| 79 | 2-naphthyl | —CH₂CH₂ | 2,3-pyridinyl | CH₂Ph | H |
| 80 | phenyl | -CH=CH- phenyl | 2,3-pyridinyl | CH₂(4-pyridyl) | phenyl |
| 81 | 2-naphthyl | -CH=CH- | 2,3-pyridinyl | CH₂(4-pyridyl) | phenyl |
| 82 | phenyl | —CH₂S— phenyl | 2,6-pyrazinyl | CH₂Ph | H |
| 83 | phenyl | —CH₂S— phenyl | 2,6-pyrazinyl | CH₂Ph | CONH₂ |
| 84 | phenyl | —CH₂SO₂— phenyl | 2,6-pyrazinyl | CH₂Ph | CONH₂ |
| 85 | phenyl | —CH₂SO₂— phenyl | 2,6-pyrazinyl | CH₂Ph | H |

Example 86

2-(4,6-Dimethoxypyrimidin-1-yl)oxy-N-(3-phenylpropan-1-al-2-yl)-quinoline-4-carboxamide MS: m/e=458 (M⁺)

Example 87

N-(3-Phenylpropan-1-al-2-yl)-2-(2-pyridyl)oxy-8-trifluoromethy-quinoline-4-carboxamide $^1$H-NMR (D$_6$-DMSO): δ=3.0(1H), 3.4(1H), 4.9(1H), 7.3–8.9 (13H), 9.5(1H) and 9.9(1H) ppm.

Example 88

N-(3-Phenylpropan-1-al-2-yl)-2-(naphtho[c]pyrimidion-3-yl)-5-nicotinamide $^1$H-NMR (CF$_3$COOD): δ=3.1–3.4(2H), 4.8(1H), 6.7(1H), 7.1–8.3(12H), 8.7(1H) and 8.9(1H) ppm.

Example 89

N-(3-Chlorophenyl)carbamoyl-6-methyl-N-(3-phenylpropan-1-al-2-yl)-pyridine-3-carboxamide $^1$H-NMR (CF$_3$COOD): δ=2.0–2.7(2H), 2.95(1H), 3.3–4.0 (6H), 5.9(1H), 6.9(1H), 7.0–7.5(10H) and 7.9(1H) ppm.

We claim:
1. An amide of the general formula I

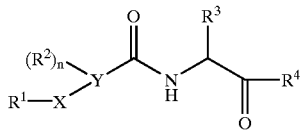

and its tautomeric and isomeric forms, possible enantiomeric and diastereomeric forms, as well as possible physiologically tolerable salts, in which the variables have the following meanings:

R$^1$ is selected from the group consisting of phenyl, naphthyl, quinolyl, pyridyl, pyrimidyl, pyrazyl, pyridazyl, imidazolyl, thiazole, quinazyl, isoquinolyl, quinazyl, quinoxalyl, thienyl, benzothienyl, benzofuranyl, furanyl, and indolyl, where the rings can be additionally substituted by up to 3 radicals R$^5$, R$^2$ is selected from the group consisting of chlorine, bromine, fluorine, C$_1$–C$_6$-alkyl, C$_1$–C$_6$-alkenyl, C$_1$–C$_6$-alkynyl, C$_1$–C$_6$-alkylphenyl, C$_1$–C$_6$-alkenylphenyl, C$_1$–C$_6$-alkynylphenyl, phenyl, NHCO—C$_1$–C$_4$-alkyl, NHSO$_2$—C$_1$–C$_4$-alkyl, —NHCOphenyl —NHCO-naphthyl, NO$_2$, —O—C$_1$–C$_4$-alkyl and NH$_2$, where the aromatic rings can additionally carry one or two radicals R$^5$ and two radicals R$^2$ together can also be a chain —CH=CH—CH=CH— and thus form a fused benzo ring, which can be substituted by one R$^5$, R$^3$ is —C$_1$–C$_6$-alkyl, which is branched or unbranched, and which can additionally carry an S—CH$_3$ radical or a phenyl, cyclohexyl, cycloheptyl, cyclopentyl, indolyl, pyridyl or naphthyl ring which is substituted by at most two radicals R$^5$, where R$^5$ is selected from the group consisting of hydrogen, C$_1$–C$_4$-alkyl, which is branched or unbranched, —O—C$_1$–C$_4$-alkyl, OH, Cl, F, Br, I, CF$_3$, NO$_2$, NH$_2$, CN, COOH, COO—C$_1$–C$_4$-alkyl, —NHCO—C$_1$–C$_4$-alkyl, —NHCO-phenyl, —NHSO$_2$—C$_1$–C$_4$-alkyl, —NHSO$_2$-phenyl, —SO$_2$—C$_1$–C$_4$-alkyl, —(CH$_2$)$_n$—NR$^{12}$R$^{13}$ and —SO$_2$-phenyl, X is selected from the group consisting of a bond, —(CH$_2$)$_m$—, —(CH$_2$)$_m$—O—(CH$_2$)$_o$—, —(CH$_2$)$_o$-S—(CH$_2$)$_m$—, —(CH$_2$)$_o$—SO—(CH$_2$)$_m$—, —(CH$_2$)$_o$—SO$_2$—(CH$_2$)$_m$—, —CH=CH—, —C≡C—, —CO—CH=CH—, —(CH$_2$)$_o$—CO—(CH$_2$)$_m$—, —(CH$_2$)$_m$—NHCO—(CH$_2$)$_o$—(CH$_2$)$_m$—CONH—(CH$_2$)$_o$—, —(CH$_2$)$_m$—NHSO$_2$—(CH$_2$)$_o$—, —NH—CO—CH=CH—, —(CH$_2$)$_m$—SO$_2$NH—(CH$_2$)$_o$—, —CH=CH—CONH— and

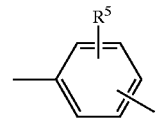

and in the case of CH=CH double bonds can be either the E or the Z form and R$^1$-X together are also

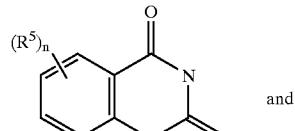

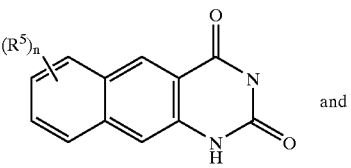

Y is pyridine, and R$^4$ is selected from the group consisting of hydrogen, COOR$^6$, CO—Z, in which Z is NR$^7$R$^8$,

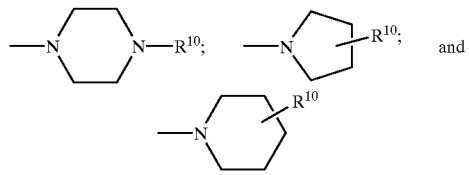

R$^6$ is hydrogen or C$_1$–C$_6$-alkyl, which is linear or branched, and which can be substituted by a phenyl ring which itself can additionally be substituted by one or two radicals R$^9$, R$^7$ is hydrogen or C$_1$–C$_6$-alkyl, which is branched and unbranched, R$^8$ is hydrogen or C$_1$–C$_6$-alkyl, which is branched or unbranched which can additionally be substituted by a phenyl ring which can additionally carry a radical R$^9$, and by

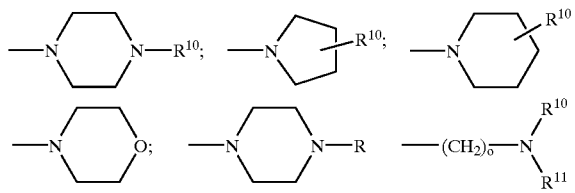

R$^9$ is selected from the group consisting of hydrogen, C$_1$–C$_4$-alkyl, which is branched or unbranched, —O—$C_1$–$C_4$-alkyl, OH, Cl, F, Br, I, $CF_3$, $NO_2$, $NH_2$, CN, COOH, COO—$C_1$–$C_4$-alkyl, —NHCO—$C_1$–$C_4$-alkyl, —NHCO-phenyl, —$NHSO_2$—$C_1$–$C_4$-alkyl, —$NHSO_2$-phenyl, —$SO_2$—$C_1$–$C_4$-alkyl and —$SO_2$-phenyl, $R^{10}$ is hydrogen or $C_1$–$C_6$-alkyl, which is linear or branched, and which can be substituted by a phenyl ring which itself can additionally be substituted by one or two radicals $R^9$, $R^{11}$ is hydrogen or $C_1$–$C_6$-alkyl, which is linear or branched, and which can be substituted by a phenyl ring which itself can additionally be substituted by one or two radicals $R^9$, n is a number 0, 1 or 2, and m and o independently of one another are each a numeral 0, 1, 2, 3 or 4.

2. An amide of the formula I as claimed in claim 1, where $R^3$ is benzyl, $CH_2CH_2CH_2CH_3$, or $CH_2CH_2CH_2CH_2CH_3$, Y is pyridine, $R^4$ is CO—$NR^7NR^8$, $R^7$ is hydrogen, $R^8$ is $CH_2CH_2$, $CH_2CH_2CH_2$, or $CH_2CH_2CH_2CH_2$, $R^9$ is hydrogen, n is 0 or 1 and all remaining variables have the same meanings as in claim 1.

3. An amide of the formula I as claimed in claim 1, where $R^3$ is benzyl, $CH_2CH_2CH_2CH_3$, or $CH_2CH_2CH_2CH_2CH_3$, Y is pyridine, $R^4$ is hydrogen, $R^9$ is hydrogen, n is 0 or 1 and all remaining variables have the same meanings as in claim 1.

4. A method of inhibiting cysteine proteases in a patient in need of such treatment comprising administering an effective amount of a compound of claim 1 to a patient in need of such treatment.

5. The method of claim 4, wherein the cysteine proteases are selected from the group consisting of calpains I and II and cathepsins B and L.

6. A method of treating neurodegenerative diseases and neuronal damage in a patient in need of such treatment comprising administering an effective amount of a compound of claim 1 to a patient in need of such treatment.

7. The method of claim 6 where the neorodegenerative diseases and neuronal damage is caused by ischemia, trauma or mass hemorrhages.

8. The method of claim 6 for the treatment of cerebral stroke and craniocerebral trauma.

9. The method of claim 6 wherein the disease is Alzheimer's disease or Huntington's disease.

10. The method of claim 6 wherein the disease is epilepsy.

11. A method of treating damage to the heart after cardiac ischemias, reperfusion damage after vascular occlusion, damage to the kidneys after renal ischemias, skeletal muscular damage, muscular dystrophies, damage which results due to proliferation of the smooth muscle cells, coronary vasospasm, cerebral vasospasm, cataracts of the eyes or restenosis of the blood vessels after angioplasty comprising administering an effective amount of a compound of claim 1 to a patient in need of such treatment.

12. A method of treating tumors and metastasis thereof comprising administering an effective amount of a compound of claim 1 to a patient in need of such treatment.

13. A method of treating diseases in which increased interleukin-1 levels occur comprising administering an effective amount of a compound of claim 1 to a patient in need of such treatment.

14. A method of treating inflammation and rheumatic disorders comprising administering an effective amount of a compound of claim 1 to a patient in need of such treatment.

15. A pharmaceutical composition for oral, parenteral and intraperitoneal use, comprising a compound of claim 1 and a pharmaceutically acceptable carrier.

\* \* \* \* \*